United States Patent [19]

Toan et al.

[11] Patent Number: 5,509,957
[45] Date of Patent: Apr. 23, 1996

[54] INK COMPOSITIONS

[75] Inventors: Vien V. Toan, Lentigny; Hugh S. Laver, Reinach; David G. Leppard, Marly, all of Switzerland

[73] Assignee: Ciba-Geigy Corporation, Tarrytown, N.Y.

[21] Appl. No.: 147,706

[22] Filed: Nov. 4, 1993

[30] Foreign Application Priority Data

Nov. 9, 1992 [CH] Switzerland .............. 3456/92

[51] Int. Cl.$^6$ .................... C09D 11/16
[52] U.S. Cl. ............... 106/20 R; 106/20 D; 106/22 R
[58] Field of Search ................ 106/20 D, 20 R, 106/22 R

[56] References Cited

U.S. PATENT DOCUMENTS

| | | | |
|---|---|---|---|
| 5,073,448 | 12/1991 | Vieira et al. | 428/331 |
| 5,089,050 | 2/1992 | Vieira et al. | 106/20 D |
| 5,098,477 | 3/1992 | Vieira et al. | 106/20 R |
| 5,261,953 | 11/1993 | Vieira et al. | 106/20 R |

FOREIGN PATENT DOCUMENTS

| | | |
|---|---|---|
| 63-128085 | 5/1988 | Japan. |
| 2088777 | 6/1982 | United Kingdom. |

OTHER PUBLICATIONS

Chem. Abst. 109:212533v of Jp 63-128085 1988 no month.
Chem abstract 96:105780 Biswas et al. "A carbazole-based polymeric azodye", J. Polym. Sci, 19 (12), 3155–64 (1981) (no month).
Chem abstract 85:79669 of PL 78531, Jun. 1975 to Kozlowski et al., "Yellow azo dye for fiber".
CA 85:20849 Oligomeric condensation products of p-cresolsulfonic acid with formaldehyde. Gedeon, J. et al., DE 2444785, Apr. 1976.
CA 80:143786 Polycresolsulfonic acids., of DE 2245411 Mar. 1974.
CA Registry No. 7355-35-3 (no date available).
CHEMLIST ascension Nos. 139908 and 133924, both 1990 (no month).
CA registry No. 85433-47-6 (no date available).
CA registry No. 82919-38-8 (no date available).
CA registry No. 93917-84-1 (no date available).
CA registry No. 106593-15-1 (no date available).

*Primary Examiner*—Mark L. Bell
*Assistant Examiner*—Scott L. Hertzog
*Attorney, Agent, or Firm*—Luther A. R. Hall; Michele A. Kovaleski

[57] ABSTRACT

The invention relates to ink compositions, in particular for ink-jet printing, containing as stabiliser a water-soluble compound of formula

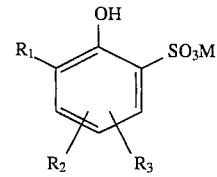

or

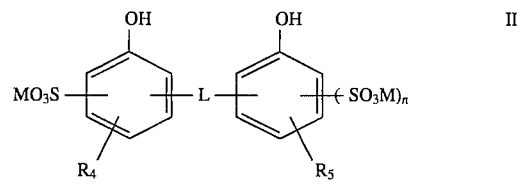

wherein $R_1$, $R_2$, $R_3$, $R_4$, $R_5$, L, M and n are as defined in claim 1, to said compounds and to recording materials containing them, and to a process for stabilising ink-jet prints, the stabiliser being a compound of formula (I) or (II).

11 Claims, No Drawings

INK COMPOSITIONS

The present invention relates to novel ink compositions, in particular those suitable for ink-jet printing.

Inks, including those suitable for ink-jet printing, usually contain water-soluble dyes. Without exception, however, the lightfastness of these water-soluble dyes is inferior to that of the coloured pigments used in conventional printing methods. As a consequence, the prints have only a limited storage life when exposed to light. When exposed to light during prolonged storage they begin to bleach or discolour.

To solve this problem the proposal has been made, inter alia in JP-A-63-128 085, to provide phenols which are sulfonated in para-position to the OH group, for example the lithium salt of 3,5-di-tert-butyl-4-hydroxyphenylsulfonic acid.

This invention now provides other more effective phenols which are very suitable for use in ink compositions and are thus able to stabilise the prints obtained therewith.

Accordingly, the invention relates to an ink composition comprising at least one water-soluble compound of formula

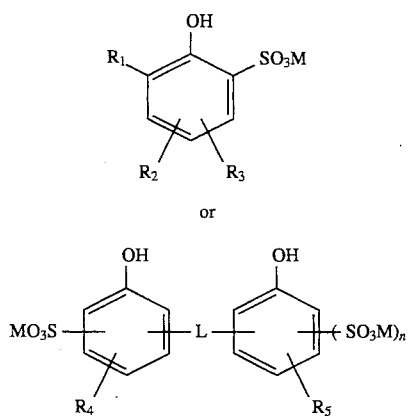

wherein $R_1$ is H, $C_1$–$C_{18}$alkyl, $C_7$–$C_9$phenylalkyl, phenyl or a group of formula III

$R_2$ is H, $C_1$–$C_{18}$alkyl, $C_7$–$C_9$phenylalkyl, phenyl, a group of formula III or group of formula IV —$CH_2CH_2COOR_6$ (IV);

$R_3$ is H, $C_1$–$C_4$alkyl;

M is H, an alkali metal ion or a group $(R_7)(R_8)(R_9)(R_{10})N$;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is a direct bond, —$C(R_{11})(R_{12})$— or —S—;

wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring, each unsubstituted or substituted by 1 to 3 $C_1$–$C_4$alkyl groups;

$R_4$ and $R_5$ are each independently of the other H or $C_1$–$C_8$alkyl;

$R_6$ is M, unsubstituted $C_1$–$C_4$alkyl or $C_1$–$C_4$alkyl which is substituted by one —OH group, or is $C_3$–$C_{20}$alkyl which is interrupted by one or more than one oxygen atom; and n is 0 or 1.

The invention also relates to a recording material comprising at least one compound of formula (I) or (II), to a process for stabilising ink-jet prints, and to the novel compounds of formulae (I) and (II).

Substituents in the novel stabilisers defined as alkyl of up to 18 carbon atoms are suitably methyl, ethyl, propyl, butyl, pentyl, hexyl, octyl, decyl, dodecyl, tetradecyl, hexadecyl and octadecyl as well as corresponding branched isomers. Alkyl groups of shorter chain, typically $C_1$–$C_5$alkyl, are preferred for use in aqueous inks.

Substituents in the novel stabilisers defined as $C_7$–$C_9$phenylalkyl are suitably benzyl and cumyl.

Substituents in the novel stabilisers defined as $C_3$–$C_{20}$alkyl which is interrupted by one or more than one oxygen atom are suitably —$[(CH_2)_2$—$O]_{2-9}$—$CH_3$ or —$[(CH_2)_2$—$O]_{2-9}$—$CH_2CH_3$.

Substituents in the novel stabilisers defined as alkali metal ions are suitably $Li^{\oplus}$, $Na^{\oplus}$ and $K^{\oplus}$.

The novel ink compositions are distinguished by good stability to light. They may be typically used for felt-tipped pens, ink pads, fountain pens and pen plotters, as well as for offset, book, flexographic and intaglio printing, and also for typewriter ribbons for dot matrix and calligraphic printing. The preferred utility is for ink jet printing.

Among the printers used for current ink-jet printing techniques, a distinction is made between continuous ink-jet and drop-on-demand printers, especially bubble-jet printers. The ink compositions of this invention are suitable for use with these printers. It is preferred to print ink jet papers and sheets.

The novel ink compositions may contain water-soluble solvents such as ethylene glycol, diethylene glycol, triethylene glycol or higher ethylene glycols, propylene glycol, 1,4-butanediol, or ethers of such glycols, thiodiglycol, glycerol and the ethers and esters thereof, polyglycerol, mono-, di- and triethanolamine, propanolamine, dimethyl formamide, dimethyl sulfoxide, dimethyl acetamide, N-methylpyrrolidone, 1,3-dimethylimidazolidone, methanol, ethanol, isopropanol, n-propanol, diacetone alcohol, acetone, methyl ethyl ketone or propylene carbonate.

The novel ink compositions also contain the dyes used for colouring natural fibres. These dyes may typically be mono-, di- or polyazo dyes, reactive dyes, triphenylmethane dyes, xanthene dyes or phthalocyanine dyes. Specific examples of such dyes are Food Black 2, C.I. Direct Black 19, C.I. Sulphur Black 1, Acid Red 35, Acid Red 14, Acid Red 52, Acid Yellow 17, Acid Yellow 23 and copper phthalocyanines, also Direct Black 38, Direct Black 168, Acid Red 249, Direct Red 227, Direct Yellow 86, Direct Yellow 132, Acid Blue 9, Direct Blue 86 and Direct Blue 199 as well as Reactive Red 24, Reactive Red 40 and Reactive Red 159 and the azo dyes listed in EP-A-366 121.

The ink compositions may also contain minor amounts of conventional modifiers such as binders, surfactants, biocides, corrosion inhibitors, sequestrants, pH buffers or conductivity additives. They may also contain further UV absorbers or light stabilisers, including the compounds disclosed in U.S. Pat. No. 5,073,448, U.S. Pat. No. 5,089,050 or, in particular, in U.S. Pat. No. 5,096,489 and U.S. Pat. No. 5,124,723. Normally, however, the addition of one of the stabilisers of formula (I) or (II) to the ink composition will suffice in the practice of this invention.

Ink-jet printing compositions are also known which consist of more than one phase. Ink compositions that consist of an aqueous phase in which the dye is dissolved and an emulsion of oil drops that contains the UV absorbers and optional antioxidants are disclosed in JP-A-0 1170 675, 0 1182 379, 0 1182 380, 0 1182 381 and 0 1193 376. In JP-A-0 1170 673 and 0 1182 382 the oil phase containing the UV absorbers is microencapsulated and the dye is dissolved in the aqueous phase. Oil-soluble dyes, however, can be dissolved in an oil together with UV absorbers and optional antioxidants. The oil is either emulsified or dispersed in an aqueous phase as described, inter alia, in JP-A-0 1170 674 and 0 1170 672. The compounds of formulae (I) and (II) are very suitable for stabilising such ink compositions. They are water-soluble and can be dissolved in the aqueous phase.

The novel ink compositions preferably contain 0.01–30% by weight, most preferably 0.1–20% by weight, of a compound of formula (I) or (II).

Preferred ink compositions contain a compound of formula

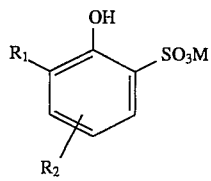           (I')

or

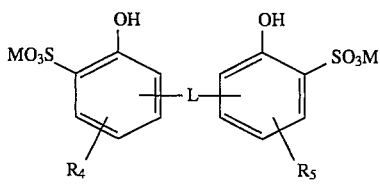           (II')

wherein
$R_1$ is H, $C_1$–$C_8$alkyl,

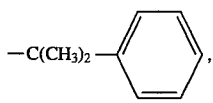, phenyl or a group of formula III

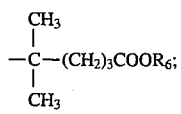           (III)

$R_2$ is H, $C_1$–$C_{12}$alkyl or a group of formula IV
—$CH_2CH_2COOR_6$ (IV), M is H, an alkali metal ion or $NH_4$, L is a direct bond or —$C(R_{11})(R_{12})$—,
  wherein $R_{11}$ and $R_{12}$ are each independently of the other H, $C_1$–$C_4$alkyl, or $R_{11}$ and $R_{12}$, together with the linking carbon atom, form a cyclopentylene or cyclohexylene ring which is unsubstituted or substituted by 1 to 3 $C_1$–$C_4$alkyl groups;

$R_4$ and $R_5$ are each independently of the other H, $C_1$–$C_4$alkyl; and $R_6$ is H or $C_1$–$C_4$alkyl.

Also preferred are ink compositions containing compounds of formula (I') or (II'), wherein $R_1$ is H or $C_1$–$C_4$alkyl;
$R_2$ is H or $C_1$–$C_8$alkyl;
M is Li;

L is —$C(R_{11})(R_{12})$—
  wherein $R_{11}$ and $R_{12}$ are each independently of the other H, $C_1$–$C_4$alkyl or $R_{11}$ and $R_{12}$, together with the linking carbon atom, form a cyclohexylene ring; and $R_4$ and $R_5$ are each independently of the other H or $C_1$–$C_4$alkyl.

Very suitable ink compositions are also those wherein the stabiliser is a compound of formula

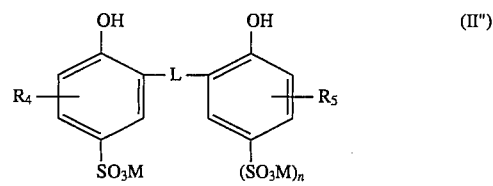           (II'')

wherein M is H, an alkali metal ion or a group $(R_7)(R_8)(R_9)(R_{10})N$;
  wherein $R_7$, $R_8$, $R_9$ and $R_{10}$ are each independently of one another H, unsubstituted $C_1$–$C_4$alkyl or $C_1$–$C_4$alkyl which substituted by 1 to 3 —OH groups, $C_3$–$C_{20}$alkyl which is interrupted by one or more than one oxygen atom, or are allyl, cyclopentyl, cyclohexyl, phenyl, benzyl or tolyl;

L is direct bond, —$C(R_{11})(R_{12})$— or —S—;
  wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring which is unsubstituted or substituted by 1 to 3 $C_1$–$C_4$alkyl groups;

$R_4$ and $R_5$ are are each independently of the other H, $C_1$–$C_8$alkyl; and n is 0 or 1.

Illustrative examples of water-soluble compounds of formula (I) or (II) suitable for use in recording materials and inks are the following compounds 1–30:

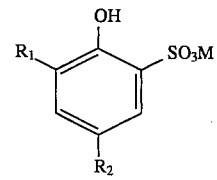

| Cmpd. No. | $R_1$ | $R_2$ | M |
|---|---|---|---|
| 1 | $C(CH_3)_3$ | $C(CH_3)_3$ | Li |
| 2 | $CH(CH_3)C_2H_5$ | $C(CH_3)_3$ | Li |
| 3 | $C(CH_3)_3$ | $CH_3$ | Li |
| 4 | $C(CH_3)_3$ | $CH_3$ | Na |
| 5 | $C(CH_3)_2C_6H_5$ | $CH_3$ | Li |
| 6 | $CH_3$ | $CH_3$ | Li |
| 7 | $CH_3$ | $CH_3$ | Na |
| 8 | $C(CH_3)_2(CH_2)_3COOCH_3$ | $CH_3$ | Li |
| 9 | H | $C(CH_3)_3$ | Li |
| 10 | H | $CH(CH_3)C_2H_5$ | Li |
| 11 | H | $C(CH_3)_2C_2H_5$ | Li |
| 12 | H | $C_9H_{19}$ | Li |
| 13 | H | $C_{12}H_{25}$ | Li |
| 14 | $C(CH_3)_3$ | $CH_2CH_2COOCH_3$ | Li |

| Cmpd. No. | Structure |
|---|---|
| 15 | 2-SO₃Li, 4,6-di-CH₃ phenol (OH with SO₃Li ortho, CH₃ at 4 and 6) |

Structure for compounds 16–18:

LiO₃S—[phenol(OH)-R₄]—L—[phenol(OH)-R₅]—SO₃Li

| Cmpd. No. | L | R₄ = R₅ |
|---|---|---|
| 16 | —CH(CH₃)— | C(CH₃)₃ |
| 17 | bond | C(CH₃)₃ |
| 18 | bond | CH₃ |

Structure for compounds 19–27:

HO₃S—[HO-phenyl-R₄]—L—[phenyl(SO₃H)(OH)-R₅]—

| Cmpd. No. | L | R₄ = R₅ | M |
|---|---|---|---|
| 19 | —C(CH₃)₂— | H | Li |
| 20 | —C(CH₃)₂— | H | K |
| 21 | cyclohexylidene | CH₃ | Li |
| 22 | cyclohexylidene | CH(CH₃)₂ | Li |
| 23 | cyclohexylidene | C(CH₃)₃ | Li |
| 24 | cyclohexylidene | C(CH₃)₃ | Na |
| 25 | 3,3,5-trimethylcyclohexylidene | CH₃ | Li |
| 26 | 4-methylcyclohexylidene | C(CH₃)₃ | Li |
| 27 | 4-methylcyclohexylidene | C(CH₃)₃ | Li |
| 28 | cyclopentylidene | CH₃ | Li |

Structure for compounds 29–30:

2,2'-biphenol with LiO₃S on one ring and (SO₃Li)ₙ on the other

| Cmpd. No. | n |
|---|---|
| 29 | 0 |
| 30 | 1 |

Very particularly preferred ink compositions are those that contain compounds (15), (19) or (21).

The compounds can be readily incorporated in ink compositions and recording materials. Where a compound of formula (I) or (II) is in the form of an acid, it can be neutralised with a base such as lithium or ammonium hydroxide.

The recording materials of this invention, which are preferably used for ink-jet printing and which contain a compound of formula (I) or (II), consist of a substrate having a surface which is printable by means of an ink jet. The substrate is usually paper or a plastic sheet and is normally coated on one side with a material which is able to absorb ink. This layer will preferably contain $SiO_2$ and polyvinyl alcohol.

Uncoated paper can also be used. In this case, the paper acts simultaneously as substrate and ink absorbing layer. Materials made of cellulosic fibres and textile fibre materials such as cotton fabric or blends of cotton and polyacrylamide or polyester, which materials contain a compound of formula (I) or (II), can also be used for ink-jet printing.

The recording materials can also be transparent, as in the case of projection transparencies.

The compound of formula (I) or (II) can be incorporated in the substrate during the preparation thereof, conveniently by addition to the pulp during paper manufacture. A second method of application comprises spraying the substrate with a solution of the compound of formula (I) or (II). The solution is in this case an aqueous solution or a solution in a readily volatile organic solvent. Spraying or impregnating the material with an organic solution of a compound of formula (I) or (II) is especially suitable when using an oil-soluble compound of formula (I) or (II). The use of emulsions or dispersions is also possible.

Normally, however, a coating composition having affinity for dyes is applied to the substrate and the compound of formula (I) or (II) is added to this composition. The coating compositions normally consist of a solid filler, a binder and conventional additives.

The filler constitutes the bulk of the coating composition. Examples of suitable fillers are $SiO_2$, kaolin, talcum, clay, calcium, magnesium or aluminium silcates, gypsum, zeolite, bentonite, diatomaceous earth, vermiculite, starch or the surface-modified $SiO_2$ described in JP-A 60-260 377. Minor amounts of white pigments such as titanium dioxide, barytes, magnesium oxide, lime, chalk or magnesium carbonate can be used with the filler in the coating composition, provided they do not drastically lower the density of the ink jet print.

Coating compositions suitable for transparent projectable recording materials may not contain any light-scattering particles such as pigments and fillers.

The binder binds the fillers to one another and to the substrate. Typical conventional binders are water-soluble polymers such as polyvinyl alcohol, partially hydrolysed polyvinyl acetate, cellulose ethers, polyvinyl pyrrolidone and copolymers thereof, polyethylene oxide, salts of polyacrylic acid, sodium alginate, oxidised starch, gelatin, casein, vegetable gum, dextrin, albumin, dispersions and polyacrylates or acrylate/methacrylate copolymers, lattices of natural or synthetic rubber, poly(meth)acrylamide, polyvinyl ethers, polyvinyl esters, copolymers of maleic acid, melamine resins, urea resins or the chemically modified polyvinyl alcohols disclosed in JP-A 61-134 290 or JP-A 61-134 291.

An additional dye receptor or a mordant which enhances the fixation of the dye to the coating may be added to the binder. Dye receptors for acid dyes are cationic or amphoteric. Exemplary cationic receptors are polymeric ammonium compounds such as polyvinylbenzyltrimethylammonium chloride, polydiallyldimethylammonium chloride, polymethacryloxyethyldimethylhydroxyethylammonium chloride, polyvinylbenzylmethylimidazolium chloride, polyvinylbenzylpicolinium chloride or polyvinylbenzyltributylammonium chloride. Further examples are basic polymers such as poly(dimethylaminoethyl)methacrylate, polyalkylenepolyamines and their condensation products with dicyandiamide, amine/epichlorohydrin polycondensates disclosed in JP-A-57-36 692, 57-64 591, 57-187 289, 57-191 084, 58-177 390, 58-208 357, 59-20 696, 59-33 176, 59-96 987, 59-198 188, 60-49 990, 60-71 796, 60-72 785, 60-161 188, 60-187 582, 60-189 481, 60-189 482, 61-14 979, 61-43 593, 61-57 379, 61-57 380, 61-58 788, 61-61 887, 61-63 477, 61-72 581, 61-95 977, 61-134 291 or in U.S. Pat. Nos. 4,547,405 and 4,554,181 as well as in DE-A-3 417 582. An amphoteric dye receptor is, for example, gelatin.

The coating having affinity for dyes may contain a number of other additives such as antioxidants, further light stabilisers (also including UV absorbers), viscosity improvers, fluorescent whitening agents, biocides and/or antistatic agents.

Illustrative examples of particularly suitable antioxidants are sterically hindered phenols, hydroquinones and hydroquinone ethers, for example the antioxidants disclosed in GB-A-2 088 777 or JP-A-60-72 785, 60-72 786 and 60-71 796.

Illustrative examples of particularly suitable light stabilisers are organic nickel compounds and sterically hindered amines, for example the light stabilisers disclosed in JP-A-58-152 072, 61-146 591, 61-163 886, 60-72 785 and 61-146 591 or in GB-A-2 088 777, JP 59-169 883 and 61-177 279.

Suitable UV absorbers which may be added to a coating composition in conjunction with a compound of formula (I) or (II) are disclosed, inter alia, in Research Disclosure No. 24 239 (1984) page 284, GB-A-2 088 777 and EP-A-0 280 650. Suitable UV absorbers for concurrent use with a compound of formula (I) or (II) in recording substrates for ink jet printing are in particular those of the 2-hydroxyphenylbenzotriazole class and, most particularly, 2-(2'-hydroxy-3',5'-di-tert-amylphenyl)benzotriazole and 2-(2'-hydroxy-3'-tert-butyl-5'-polyglycolpropionate-phenyl)benzotriazole. The UV absorbers can be added to the coating composition as emulsion or dispersion.

If the compound of formula (I) or (II) is a salt, it can be dissolved either direct in the coating composition or added thereto in the form of an emulsion or suspension. If the compound of formula (I) or (II) is an acid, it can be dissolved in the coating composition by addition of alkali.

The coating composition is usually applied to the substrate, typically paper, and dried by heating. As already mentioned, the compound of formula (I) or (II) can be also applied to the recording substrate in a separate operation, alone or together with other already described components, as an aqueous solution. Application can be made by spraying, by sizing in a sizing press, by a separate coating operation or by immersion in a vat. After subjecting the recording substrate to such an aftertreatment, an additional drying step is necessary.

The recording substrate preferably contains 1 to 10,000 mg/m$^2$, most preferably 50 bis 2000 mg$^2$, of at least one compound of formula (I) or (II).

The invention further relates to compounds of formulae (I) and (II). Preferred compounds correspond to those referred to in connection with the preferred ink compositions.

The novel compounds are very suitable stabilisers for dyes in ink compositions, especially ink compositions for ink-jet printing, as well as for the prints obtained therewith.

The novel acids can be prepared in per se known manner, conveniently by sulfonation of phenol derivatives, which sulfonation may also be carried out in conjunction with a dealkylation.

The invention is illustrated by the following non-limitative Examples. Unless otherwise stated, parts and percentages are by weight, as also in the remainder of the specification.

EXAMPLE 1

Ink-jet compositions are prepared by dissolving 2 g of dye in 5 g of diethylene glycol and 93 g of deionised water. The compositions are then filtered through an ultrafilter having a pore width of 0.45 μm. The dyes used are C.I. Acid Yellow 23 and C.I. Acid Red 249.

Each stabiliser is weighed in an amount of 0.15 g into a test tube and dissolved in 2.85 g of ink.

A Hewlett Packard "Desk-Jet" ink cartridge is emptied, washed and dried with pressurised air. A fresh cottonwool pad is placed in the empty cartridge and impregnated with the test ink composition.

Specimens having a density of 200 dots per inch are printed on photocopying paper supplied by Mühlebach (Switzerland).

After storage for 1 week to dry out the print completely, the colour density (intensity) of the specimen prints is measured with a Macbeth TR 924 densitometer. The specimen prints are then irradiated in an Atlas Weather-O-Meter with a xenon lamp having a light intensity of 81 klux behind a filter of 6 mm thick window glass. The colour density is measured once more to ascertain the percentage loss of intensity.

The results are summarised in the following table. Lower values denote higher lightfastness. The light energies, expressed in kJ/cm$^2$, refer to the wavelength range from 300 to 800 nm.

TABLE 1

| Specimen | Stabiliser Cmpd. No. | Loss of colour density (%) Acid Yellow 23 after 15 kJ/cm$^2$ |
|---|---|---|
| 1 | none | 36 |
| 2 | 15 | 12 |
| 3 | 19 | 14 |
| 4 | 29 | 4 |
| 5 | 30 | 7 |

TABLE 2

| Specimen | Stabiliser Cmpd. No. | Loss of colour density (%) Acid Red 249 after 15 kJ/cm$^2$ |
|---|---|---|
| 6 | none | 70 |
| 7 | 1 | 34 |
| 8 | 2 | 34 |
| 9 | 3 | 39 |
| 10 | 5 | 37 |
| 11 | 6 | 38 |
| 12 | 8 | 38 |
| 13 | 9 | 39 |
| 14 | 10 | 37 |
| 15 | 11 | 28 |
| 16 | 12 | 27 |
| 17 | 13 | 35 |
| 18 | 16 | 33 |
| 19 | 17 | 35 |
| 20 | 22 | 38 |
| 21 | 23 | 37 |

EXAMPLE 2

An ink-jet printing paper is prepared by weighing 20.0 g of a 5% solution of R-Polymer 1130 (modified polyvinyl alcohol, supplied by Kuraray) into a glass beaker, then adding 8.0 g of demineralised water and mixing the contents. Then 4.0 g of Silica 244 (supplied by W. R. Grace & Co.) are weighed and stirred into the mixture with a glass rod. The mixture is thereafter dispersed by ultrasonication and filtered under vacuum through a polyester cloth filter of mesh 24 μm supplied by Schweizerische Seidengazenfabrik.

The coating mixture is then coated on to ink-jet printing substrates to a thickness of 24 μm with a wire coil applicator. After drying with warm air, the coating has a dry weight of c. 4.0 g/m$^2$.

The ink-jet printing paper so obtained is printed with ink compositions containing stabiliser as described in Example 1 and tested. The results are summarised in Tables 3 and 4.

TABLE 3

| Specimen | Stabiliser Cmpd. No. | Loss of colour density (%) Acid Yellow 23 after 15 kJ/cm$^2$ |
|---|---|---|
| 22 | none | 58 |
| 23 | 15 | 32 |

TABLE 4

| Specimen | Stabiliser Cmpd. No. | Loss of colour density (%) Acid Red 249 after 15 kJ/cm$^2$ |
|---|---|---|
| 24 | none | 67 |
| 25 | 1 | 28 |

TABLE 4-continued

| Specimen | Stabiliser Cmpd. No. | Loss of colour density (%) Acid Red 249 after 15 kJ/cm$^2$ |
|---|---|---|
| 26 | 10 | 23 |
| 27 | 11 | 22 |
| 28 | 12 | 25 |

EXAMPLE 3

In a further test, an ink-jet printing paper that contains mordant is prepared by weighing 0.741 g of Polyfix 601 mordant (quaternised polyamine) supplied by Showa Polymer Co. into a 100 g glass beaker, then adding 15.04 g of demineralised water and mixing the contents. Then 20.0 g of a 5% solution of R-Polymer 1130 (supplied by Kuraray) are weighed and added. Then 4.0 g of Silica 244 (supplied by W. R. Grace & Co.) are weighed and stirred into the mixture with a glass rod. The mixture is thereafter dispersed by ultrasonication and filtered under vacuum through a polyester cloth filter of mesh 24 μm supplied by Schweizerische Seidengazenfabrik. The coating mixture is then coated on to ink-jet printing substrates with a 30 μm wire coil applicator and dried.

The papers are printed and tested as described in Example 1. The results are summarised in Tables 5 and 6.

TABLE 5

| Specimen | Stabiliser Cmpd. No. | Loss of colour density (%) Acid Yellow 23 after 7.5 kJ/cm$^2$ |
|---|---|---|
| 29 | none | 84 |
| 30 | 15 | 28 |
| 31 | 30 | 25 |

TABLE 6

| Specimen | Stabiliser Cmpd. No. | Loss of colour density (%) Acid Red 249 after 7.5 kJ/cm$^2$ |
|---|---|---|
| 32 | none | 81 |
| 33 | 10 | 35 |
| 34 | 11 | 35 |
| 35 | 12 | 31 |
| 36 | 15 | 35 |
| 37 | 19 | 34 |
| 38 | 21 | 37 |

What is claimed is:

1. An ink composition containing as stabiliser at least one water-soluble compound of formula

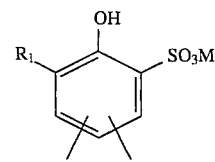

I or

-continued

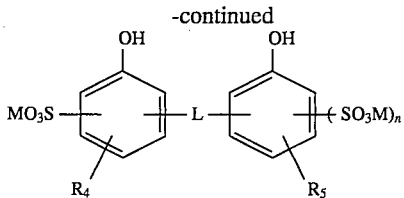
II wherein $R_1$ is H, $C_1$–$C_{18}$alkyl, $C_7$–$C_9$phenylalkyl, phenyl or a group of formula III

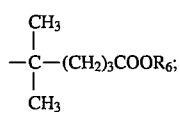
(III)

$R_2$ is H, $C_1$–$C_{18}$alkyl, $C_7$–$C_9$phenylalkyl, phenyl, a group of formula III or group of formula IV —$CH_2CH_2COOR_6$ (IV);

$R_3$ is H, $C_1$–$C_4$alkyl;

M is H, an alkali metal ion or a group $(R_7)(R_8)(R_9)(R_{10})N$;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is a direct bond, —$C(R_{11})(R_{12})$— or —S—;

wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring, each unsubstituted or substituted by 1 to 3 $C_1$–$C_4$alkyl groups;

$R_4$ and $R_5$ are are each independently of the other H or $C_1$–$C_8$alkyl;

$R_6$ is M, unsubstituted $C_1$–$C_4$alkyl or $C_1$–$C_4$alkyl which is substituted by one —OH group, or is $C_3$–$C_{20}$alkyl which is interrupted by one or more than one oxygen atom; and n is 0 or 1.

2. An ink composition according to claim 1, which contains a stabiliser of formula

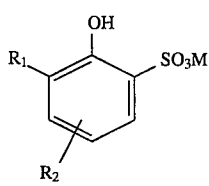
(I')

or

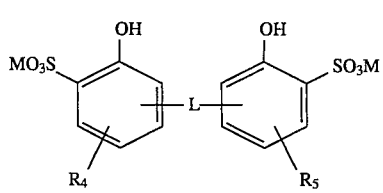
(II')

wherein $R_1$ is H, $C_1$–$C_8$alkyl,

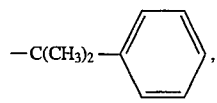

phenyl or a group of formula III

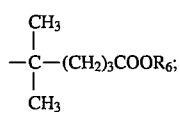
(III)

$R_2$ is H, $C_1$–$C_{12}$alkyl or a group of formula IV —$CH_2CH_2COOR_6$ (IV), M is H, an alkali metal ion or $NH_4$, L is a direct bond or —$C(R_{11})(R_{12})$—, wherein $R_{11}$ and $R_{12}$ are each independently of the other H, $C_1$–$C_4$alkyl, or $R_{11}$ and $R_{12}$, together with the linking carbon atom, form a cyclopentylene or cyclohexylene ring which is unsubstituted or substituted by 1 to 3 $C_1$–$C_4$alkyl groups;

$R_4$ and $R_5$ are each independently of the other H, $C_1$–$C_4$alkyl; and $R_6$ is H or $C_1$–$C_4$alkyl.

3. An ink composition according to claim 1, which contains a stabiliser of formula

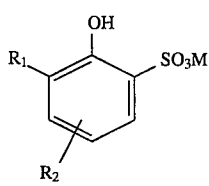

or

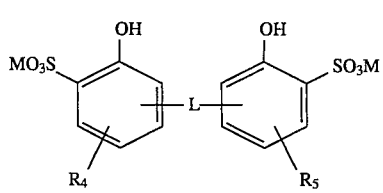

wherein $R_1$ is H or $C_1$–$C_4$alkyl;

$R_2$ is H or $C_1$–$C_8$alkyl;

M is Li;

L is —$C(R_{11})(R_{12})$— wherein $R_{11}$ and $R_{12}$ are each independently of the other H, $C_1$–$C_4$alkyl or $R_{11}$ and $R_{12}$, together with the linking carbon atom, form a cyclohexylene ring; and $R_4$ and $R_5$ are each independently of the other H or $C_1$–$C_4$alkyl.

4. An ink composition according to claim 1, which contains a stabiliser of formula

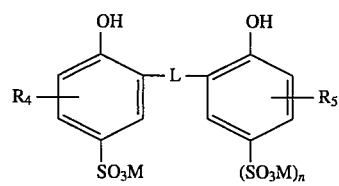
(II")

wherein M is H, an alkali metal ion or a group $(R_7)(R_8)(R_9)(R_{10})N$;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is direct bond, —C($R_{11}$)($R_{12}$)— or —S—;

wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring which is unsubstituted or substituted by 1 to 3 $C_1$–$C_4$alkyl groups;

$R_4$ and $R_5$ are are each independently of the other H, $C_1$–$C_8$alkyl; and n is 0 or 1.

5. An ink composition according to claim 1, which contains 0.01–30% by weight of at least one compound of formula (I) or (II).

6. An ink composition according to claim 1, which contains 0.1–20% by weight, of at least one compound of formula (I) or (II).

7. A recording material that contains at least one compound of formula

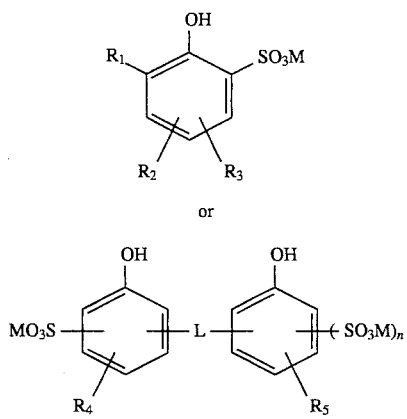

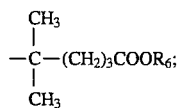

wherein $R_1$ is H, $C_1$–$C_{18}$alkyl, $C_7$–$C_9$phenylalkyl, phenyl or a group of formula III $$-\underset{\underset{CH_3}{|}}{\overset{\overset{CH_3}{|}}{C}}-(CH_2)_3COOR_6; \quad (III)$$

$R_2$ is H, $C_1$–$C_{18}$alkyl, $C_7$–$C_9$phenylalkyl, phenyl, a group of formula III or group of formula IV —$CH_2CH_2COOR_6$ (IV);

$R_3$ is H, $C_1$–$C_4$alkyl;

M is H, an alkali metal ion or a group ($R_7$)($R_8$)($R_9$)($R_{10}$)N;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is a direct bond, —C($R_{11}$)($R_{12}$)— or —S—;

wherein $R_{11}$ and $R_{12}$ are each independently of the other H or $C_1$–$C_8$alkyl;

or $R_{11}$ and $R_{12}$, together with the linking carbon atom, form a cyclopentylene, cyclohexylene or cycloheptylene ring, each unsubstituted or substituted by 1 to 3 $C_1$–$C_4$alkyl groups;

$R_4$ and $R_5$ are are each independently of the other H or $C_1$–$C_8$alkyl;

$R_6$ is M, unsubstituted $C_1$–$C_4$alkyl or $C_1$–$C_4$alkyl which is substituted by one —OH group, or is $C_3$–$C_{20}$alkyl which is interrupted by one or more than one oxygen atom; and n is 0 or 1.

8. A recording material according to claim 7 which is suitable for ink-jet printing.

9. A recording material according to claim 7, which contains 1 to 10,000 mg/m² of at least one compound of formula (I) or (II).

10. A process for stabilising ink-jet prints, which comprises applying to a recording material for ink-jet printing an ink composition in the form of an aqueous solution comprising a water-soluble dye and at least one compound of formula

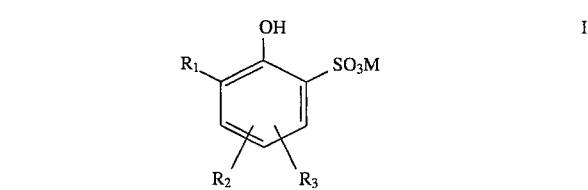

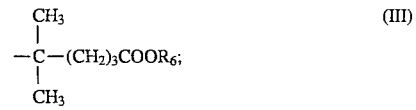

wherein $R_1$ is H, $C_1$–$C_{18}$alkyl, $C_7$–$C_9$phenylalkyl, phenyl or a group of formula III $$-\underset{\underset{CH_3}{|}}{\overset{\overset{CH_3}{|}}{C}}-(CH_2)_3COOR_6; \quad (III)$$

$R_2$ is H, $C_1$–$C_{18}$alkyl, $C_7$–$C_9$phenylalkyl, phenyl, a group of formula III or group of formula IV —$CH_2CH_2COOR_6$ (IV);

$R_3$ is H, $C_1$–$C_4$alkyl;

M is H, an alkali metal ion or a group ($R_7$)($R_8$)($R_9$)($R_{10}$)N;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is a direct bond, —C($R_{11}$)($R_{12}$)— or —S—;

wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring, each unsubstituted or substituted by 1 to 3 $C_1$–$C_4$alkyl groups;

$R_4$ and $R_5$ are each independently of the other H or $C_1$–$C_8$alkyl;

$R_6$ is M, unsubstituted $C_1$–$C_4$alkyl or $C_1$–$C_4$alkyl which is substituted by one —OH group, or is $C_3$–$C_{20}$alkyl which is interrupted by one or more than one oxygen atom; and n is 0 or 1, and drying said recording material.

11. A process for stabilising ink-jet prints, which comprises applying to a recording material for ink-jet printing that contains at least one compound of formula

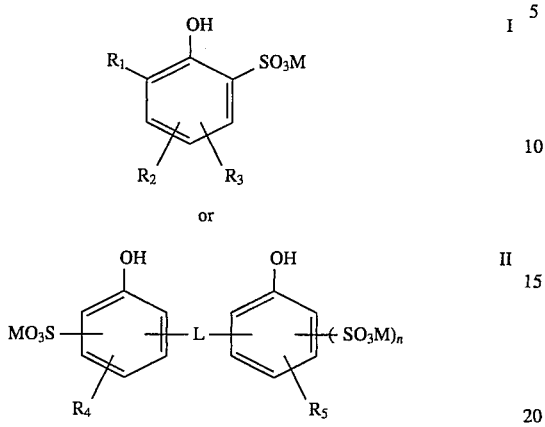

wherein $R_1$ is H, $C_1$–$C_{18}$alkyl, $C_7$–$C_9$phenylalkyl, phenyl or a group of formula III

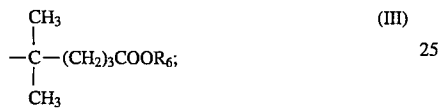

$R_2$ is H, $C_1$–$C_{18}$alkyl, $C_7$–$C_9$phenylalkyl, phenyl, a group of formula III or group of formula IV —$CH_2CH_2COOR_6$ (IV);

$R_3$ is H, $C_1$–$C_4$alkyl;

M is H, an alkali metal ion or a group $(R_7)(R_8)(R_9)(R_{10})N$;

wherein $R_7$, $R_8$, $R_9$ and $R_{10}$ are each independently of one another H, unsubstituted $C_1$–$C_4$alkyl or $C_1$–$C_4$alkyl which is substituted by 1 to 3 OH groups, $C_3$–$C_{20}$alkyl which is interrupted by one or more than one oxygen atom, or are allyl, cyclopentyl, cyclohexyl, phenyl, benzyl or tolyl;

L is a direct bond, —$C(R_{11})(R_{12})$— or —S—;

wherein $R_{11}$ and $R_{12}$ are each independently of the other H or $C_1$–$C_8$alkyl; or $R_{11}$ and $R_{12}$, together with the linking carbon atom, form a cyclopentylene, cyclohexylene or cycloheptylene ring, each unsubstituted or substituted by 1 to 3 $C_1$–$C_4$alkyl groups;

$R_4$ and $R_5$ are are each independently of the other H or $C_1$–$C_8$alkyl;

$R_6$ is M, unsubstituted $C_1$–$C_4$alkyl or $C_1$–$C_4$alkyl which is substituted by one —OH group, or is $C_3$–$C_{20}$alkyl which is interrupted by one or more than one oxygen atom; and n is 0 or 1, an ink composition in the form of an aqueous solution that contains a water-soluble dye, and drying said recording material.

* * * * *